US010925585B2

(12) United States Patent
Jong (10) Patent No.: US 10,925,585 B2
(45) Date of Patent: Feb. 23, 2021

(54) ULTRASONIC DIAGNOSTIC IMAGING SYSTEM WITH AUTOMATIC CONTROL OF PENETRATION, RESOLUTION AND FRAME RATE

(75) Inventor: Jing-Ming Jong, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 2076 days.

(21) Appl. No.: 12/562,236

(22) Filed: Sep. 18, 2009

(65) Prior Publication Data

US 2010/0010352 A1    Jan. 14, 2010

Related U.S. Application Data

(62) Division of application No. 10/596,113, filed on May 31, 2006, now abandoned.

(51) Int. Cl.
*A61B 8/00* (2006.01)
*G01S 7/52* (2006.01)
(Continued)

(52) U.S. Cl.
CPC ............ *A61B 8/585* (2013.01); *A61B 8/00* (2013.01); *A61B 8/465* (2013.01); *A61B 8/5276* (2013.01);
(Continued)

(58) Field of Classification Search
CPC .. A61B 8/08; A61B 8/00; A61B 8/585; A61B 8/465; A61B 8/5276; A61B 5/11;
(Continued)

(56) References Cited

U.S. PATENT DOCUMENTS 5,111,823 A * 5/1992 Cohen .......................... 600/443
5,215,094 A   6/1993 Franklin et al.
(Continued)

FOREIGN PATENT DOCUMENTS

WO    2000024316 A1    5/2000
WO    2003047433 A2    6/2003

OTHER PUBLICATIONS

Zhong, X., et al., "Speckle Tracking and Motion Compensation for Ultrasound-Based Lesion Localization," Ultrasound Symposium, 1997. Proceedings, 1997 IEEE Toronto, Ont., Canada Oct. 5-8, 1997, New York, NY, USA, IEEE, US, vol. 2, Oct. 5, 1997 pp. 1381-1384. XP010271555.

*Primary Examiner* — Hien N Nguyen (57) ABSTRACT

An ultrasonic diagnostic imaging system and method are presented in which the balance between image resolution and frame rate (Res/Speed) and the balance between image resolution and penetration (Pen/Gen/Res) are automatically adjusted in response to image content. A motion detector analyzes the relative motion between successive images. If the motion content is relatively high, the imaging parameters are changed in favor of relatively greater frame rate and reduced resolution. A low motion content causes the opposite adjustment. The electronic noise between successive images is also computed with a relatively high noise content (low correlation) in the far field resulting in an adjustment to penetration as by lowering the transmit frequency. A relatively low noise content causes an adjustment in favor of increased resolution.

18 Claims, 4 Drawing Sheets

(51) Int. Cl.
*A61B 8/08* (2006.01)
*A61B 5/11* (2006.01)

(52) U.S. Cl.
CPC ...... *G01S 7/52038* (2013.01); *G01S 7/52039* (2013.01); *G01S 7/52041* (2013.01); *G01S 7/52046* (2013.01); *G01S 7/52073* (2013.01); *A61B 5/11* (2013.01)

(58) Field of Classification Search
CPC ............ G01S 7/52046; G01S 7/52073; G01S 7/52038; G01S 7/52041; G01S 7/52039
USPC .......................................... 600/437
See application file for complete search history.

(56) References Cited

U.S. PATENT DOCUMENTS

| | | | |
|---|---|---|---|
| 5,474,073 A | 12/1995 | Schwartz et al. | |
| 5,485,842 A | 1/1996 | Quistgaard | |
| 5,529,070 A | 6/1996 | Augustine et al. | |
| 5,538,004 A | 7/1996 | Bamber | |
| 5,566,674 A | 10/1996 | Weng | |
| 5,653,234 A * | 8/1997 | Kim et al. | 600/437 |
| 5,720,291 A | 2/1998 | Schwartz | |
| 5,797,846 A | 8/1998 | Seyed-Bolorforosh et al. | |
| 5,833,613 A | 11/1998 | Averkiou et al. | |
| 5,873,830 A * | 2/1999 | Hossack et al. | 600/447 |
| 5,899,861 A | 5/1999 | Freimel et al. | |
| 5,908,391 A | 6/1999 | Muzilla et al. | |
| 5,910,114 A | 6/1999 | Nock et al. | |
| 5,919,138 A * | 7/1999 | Ustuner | 600/443 |
| 6,014,469 A * | 1/2000 | Eschbach | 382/261 |
| 6,117,081 A | 9/2000 | Jago et al. | |
| 6,171,246 B1 | 1/2001 | Averkiou et al. | |
| 6,186,950 B1 | 2/2001 | Averkiou et al. | |
| 6,238,345 B1 | 5/2001 | Wissler et al. | |
| 6,283,919 B1 | 9/2001 | Roundhill et al. | |
| 6,299,579 B1 | 10/2001 | Peterson et al. | |
| 6,312,384 B1 * | 11/2001 | Chiao | 600/443 |
| 6,423,003 B1 * | 7/2002 | Ustuner et al. | 600/443 |
| 6,442,289 B1 | 8/2002 | Olsson et al. | |
| 6,458,083 B1 | 10/2002 | Jago et al. | |
| 6,775,400 B1 * | 8/2004 | Zhao et al. | 382/131 |
| 7,248,749 B2 * | 7/2007 | Avinash et al. | 382/260 |
| 2002/0015517 A1 * | 2/2002 | Hwang | G06T 7/0012 382/131 |
| 2003/0028113 A1 * | 2/2003 | Gilbert et al. | 600/447 |
| 2005/0131300 A1 * | 6/2005 | Bakircioglu | A61B 8/06 600/453 |
| 2005/0197573 A1 * | 9/2005 | Roth | A61B 8/12 600/437 |
| 2005/0240105 A1 * | 10/2005 | Mast | A61B 8/14 600/443 |
| 2006/0241455 A1 * | 10/2006 | Shvarts | 600/447 |
| 2008/0051660 A1 * | 2/2008 | Kakadaris et al. | 600/454 |

* cited by examiner

ULTRASONIC DIAGNOSTIC IMAGING SYSTEM WITH AUTOMATIC CONTROL OF PENETRATION, RESOLUTION AND FRAME RATE

This invention relates to medical diagnostic imaging systems and, in particular, to diagnostic imaging systems which automatically control ultrasonic imaging for optimal tissue penetration, imaging frame rate, and image resolution.

Ultrasonic diagnostic imaging applications can differ widely in the imaging conditions encountered. When imaging the fetal heart for instance a high frame rate of display is required to accurately image the detail of a rapidly beating heart. In other applications such as the diagnosis of tumors in the liver, a high frame rate is not necessary but a high image quality (resolution) is generally preferred. In some cases the pathology being diagnosed may be deep within the patient's body. In other cases the pathology may be just beneath the skin. These widely differing conditions mean that the sonographer frequently has to change a wide variety of settings on the ultrasound system in order to acquire the best images for a given examination. It would be desirable to minimize the number of ultrasound system settings which need to be manipulated in order to set up the system for a new exam. In particular, it would be desirable for many of the manual settings of an ultrasound system to be automated when possible so that the ultrasound system would automatically optimize the operational settings of the system on the basis of the examination being performed.

In accordance with the principles of the present invention, an ultrasonic diagnostic imaging system is described which automates two of the most frequently used user settings, the Res/Speed control and the Pen/Gen/Res control. The Res/Speed control adjusts the trade-off between image quality (resolution) and frame rate (speed) by varying imaging parameters such as image line density, multiline order, and number of focal zones. The Pen/Gen/Res control adjusts the trade-off between image resolution and the depth of penetration of ultrasound through control of imaging parameters such as the transmit and receive frequencies. In an illustrated embodiment the setting of these controls is automated by sensing the amount of motion and/or noise in the anatomy being imaged. In response to the sensed image motion and/or noise, the relevant image parameters are automatically varied to obtain images which are a sensible balance of these competing factors.

Figure 1:
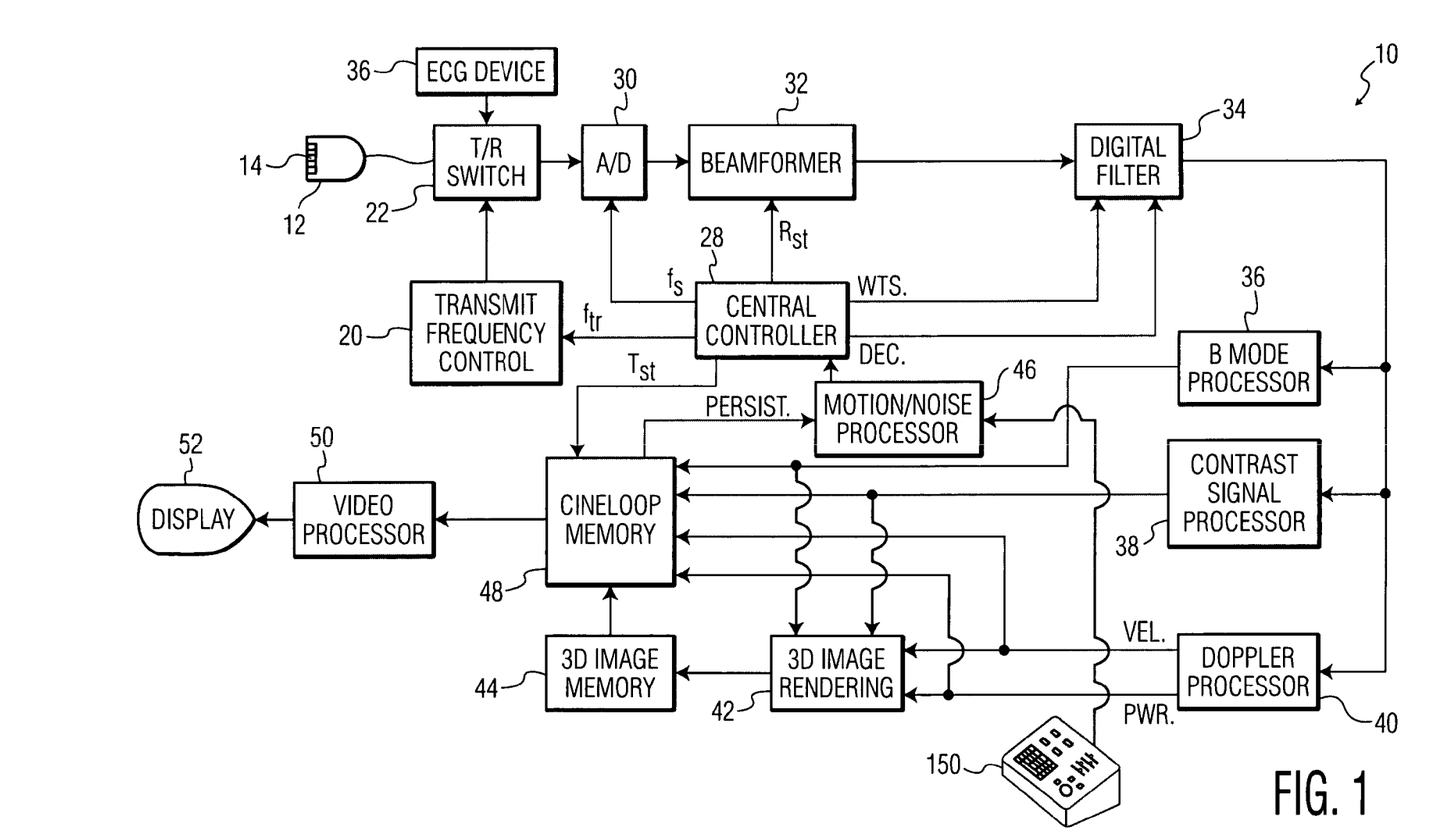
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasonic scanhead 12 includes an array 14 of ultrasonic transducers that transmit and receive ultrasonic pulses. The array may be a one dimensional linear or curved array for two dimensional imaging, or may be a two dimensional matrix of transducer elements for electronic beam steering in three dimensions. The ultrasonic transducers in the array 14 transmit ultrasonic energy and receive echoes returned in response to this transmission. A transmit frequency control circuit 20 controls the transmission of ultrasonic energy at a desired time and at a desired frequency or band of frequencies through a transmit/receive ("T/R") switch 22 coupled to the ultrasonic transducers in the array 14. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, the scanhead is commanded to acquire an ultrasonic image. The ultrasonic energy transmitted by the scanhead 12 can be relatively high energy (high mechanical index or MI) which destroys or disrupts contrast agent in the image field, or it can be relatively low energy which enables the return of echoes from the contrast agent without substantially disrupting it. The frequency and bandwidth of the ultrasonic energy generated by the transmit frequency control circuit 20 is controlled by a control signal $f_{tr}$ and the times at which individual elements in the array are actuated to steer and focus an ultrasonic beam in a desired direction is controlled by a control signal $T_{st}$. Both control signals are generated by a central controller 28.

Echoes from the transmitted ultrasonic energy are received by the transducers in the array 14, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_s$ generated by the central controller 28. The desired sampling rate dictated by sampling theory is at least twice the highest frequency of the received passband, and might be on the order of at least 30-40 MHz. Sampling rates higher than the minimum requirement are also desirable.

The echo signal samples from the individual transducers in the array 14 are delayed and summed by a beamformer 32 to form coherent echo signals in a desired beam steering direction specified by a control signal $R_{st}$. The digital coherent echo signals are then filtered by a digital filter 34. In this embodiment, the transmit frequency and the receiver frequency are individually controlled so that the beamformer 32 is free to receive a band of frequencies which is different from that of the transmitted band. The digital filter 34 bandpass filters the signals, and can also shift the frequency band to a lower or baseband frequency range. The digital filter could be a filter of the type disclosed in U.S. Pat. No. 5,833,613. Filtered echo signals from tissue are coupled from the digital filter 34 to a B mode processor 36 for conventional B mode processing. The B mode image may also be created from microbubble echoes returning in response to nondestructive ultrasonic imaging pulses.

Filtered echo signals of a contrast agent, such as microbubbles, are coupled to a contrast signal processor 38. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance. The detection and imaging of harmonic contrast signals at low MI is described in U.S. Pat. No. 6,171,246.

The filtered echo signals from the digital filter 34 are also coupled to a Doppler processor 40 for conventional Doppler processing to produce velocity and power Doppler signals. The outputs of these processors may be displayed as planar images, and are also coupled to a 3D image rendering processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference.

The signals from the contrast signal processor 38, the B-mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The sets of image data for images obtained at the same time during each of a plurality of heartbeats are preferably stored in the Cineloop memory 48 in the same way. The image data in a group can be used to display a parametric image showing tissue perfusion at a respective time during the heartbeat. The groups of image data stored in the Cineloop memory 48 are coupled to a video processor 50, which generates corresponding video signals for presentation on a display 52. The video processor 50 preferably includes persistence processing, whereby momentary intensity peaks of detected contrast agents can be sustained in the image, such as described in U.S. Pat. No. 5,215,094.

In accordance with the principles of the present invention a motion/noise processor 46 is provided to detect the motion of objects and/or noise in the image field. This is done in the illustrated embodiment by a correlation process such as a Pearson's correlation which will be discussed more fully below. The criteria against which the results of the correlation process are compared are determined by the setting of either a Res/Speed control or a Pen/Gen/Res control or both by user adjustment of a control on a user interface 150 as discussed below. The results of the detection of motion and/or noise in the image field are used to automatically adjust the settings of either or both of the Res/Speed control and the Pen/Gen/Res control. The adjustments optimize the operation of the ultrasound system to provide clearer, better resolved images by adjustment of imaging parameters in response to the outcome of the detection of motion and/or noise.

Figure 2:
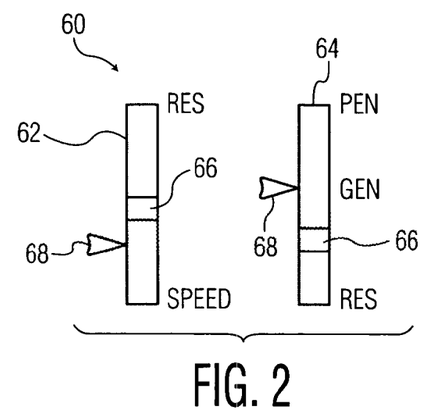
FIG. 2 illustrates an implementation of a Res/Speed control on an ultrasound system and a Pen/Gen/Res control on an ultrasound system.

Examples of a Res/Speed control and a Pen/Gen/Res control are shown in FIG. 2. While these controls may be hardware knobs or sliders on a control panel, in this embodiment the controls are display controls generated by software on the screen of the ultrasound display 52. The controls may be displayed as dials or meters or other graphics displayed in various shapes and colors, and may have either qualitative or quantitative settings. In this embodiment both are qualitative bar displays 60. The Res/Speed control 62 is variable between "Res" (maximum resolution) and "Speed" (maximum frame rate) and proportions of these maximum settings therebetween. The Pen/Gen/Res control 64 is variable between "Pen" (maximum penetration) and "Res" (maximum image resolution) and proportions of these maximum settings therebetween centered around a nominal general setting "Gen". The effect of the current setting of each control is shown by a marker 66 in the bar, which is positioned in accordance with the effective setting currently applied to the ultrasound images. An arrow 68 can be adjusted by a user pointing device such as a trackball or key or mouse on the control panel 150 to manually set a control setting.

The Res/Speed control and the Pen/Gen/Res control can be independently set for either manual control or automatic control. When a control is set for manual control its setting can only be adjusted by manual manipulation of the user. When a control is set for manual control its marker 66 is greyed out and moves in tandem with the constantly aligned arrow 68 as the user adjusts the arrow to vary the control setting. When a control is set for automatic operation its marker 66 is brightly displayed and the arrow 68 and the marker can move independently. When the user manually adjusts the arrow 68 in the automatic mode, the image will vary in response to the manual variation and the marker 66 will align with the last setting of the arrow. Once manual control of the arrow is released, automatic operation commences. As the motion and/or noise characteristic of the image field is detected and used to determine appropriate automatic settings for the Res/Speed control and/or the Pen/Gen/Res control, the marker 66 will move automatically to show the current setting resulting from automatic control. The user can see at a glance how the automatic setting has changed from his or her last manual setting, and can see the response of the control setting to the motion and noise detected in the image field.

If the user is dissatisfied with the response of the automatic operation of a control, the user can reset the position of the arrow 68 of the control. Resetting the arrow during automatic operation will reset the balance of the respective performance factors of the control and will also adjust the manner in which the automatic adjustments discussed below are made. For instance, if the user resets the arrow toward more resolution (Res), the subsequent automatic adjustments can more greatly favor changes in the direction toward a greater Res setting. Resetting the manual adjustment arrow of the controls can thus adjust the degree to which the automatic system balances the competing effects of resolution, frame rate, and depth of penetration.

Motion-detecting capabilities are often found in ultrasound systems for a variety of purposes. Various sensors have been used to detect the motion of an ultrasound probe, such as those described in U.S. Pat. No. 5,529,070 (Augustine et al.) and U.S. Pat. No. 5,538,004 (Bamber). Motion may also be sensed by comparing successive real time images as described in U.S. Pat. No. 6,299,579 (Peterson et al.); U.S. Pat. No. 6,238,345 (Wissler et al.); U.S. Pat. No. 6,117,081 (Jago et al.); U.S. Pat. No. 5,782,766 (Weng et al.); U.S. Pat. No. 5,575,286 (Weng et al.); U.S. Pat. No. 5,566,674 (Weng); U.S. Pat. No. 5,899,861 (Freimel et al.); U.S. Pat. No. 5,910,114 (Nock et al.); and WO 00/24316 (Hossack et al.) The motion sensing or image alignment techniques described in these patents are used for purposes such as aligning individual images to create a panoramic image or to remove motional distortion from images. Any one of these techniques can be used in an automated system of the present invention. In an embodiment of the present invention the motion or alignment information is used to adjust the Res/Speed setting. Higher image quality and a lower frame rate setting is employed when motion is relatively low, and lower image quality and a higher frame rate is employed when motion is relatively high.

Figure 3:
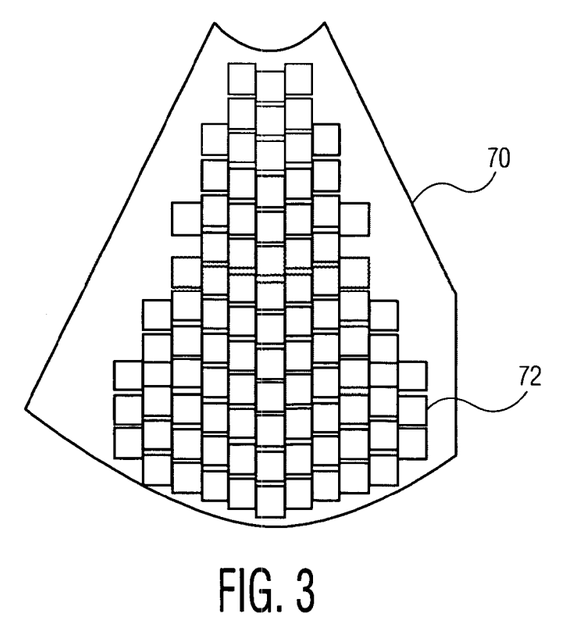
FIG. 3 illustrates an ultrasound sector image which has been divided into image sub-regions for motion analysis.

An embodiment of an automated control of the present invention can start with a sequence of ultrasound images such as image 70 in FIG. 3. Each image is analytically divided into a plurality of blocks 72 of a predetermined pixel size, such as 8 pixels by 8 pixels or 16 pixels by 16 pixels.

Figure 4:
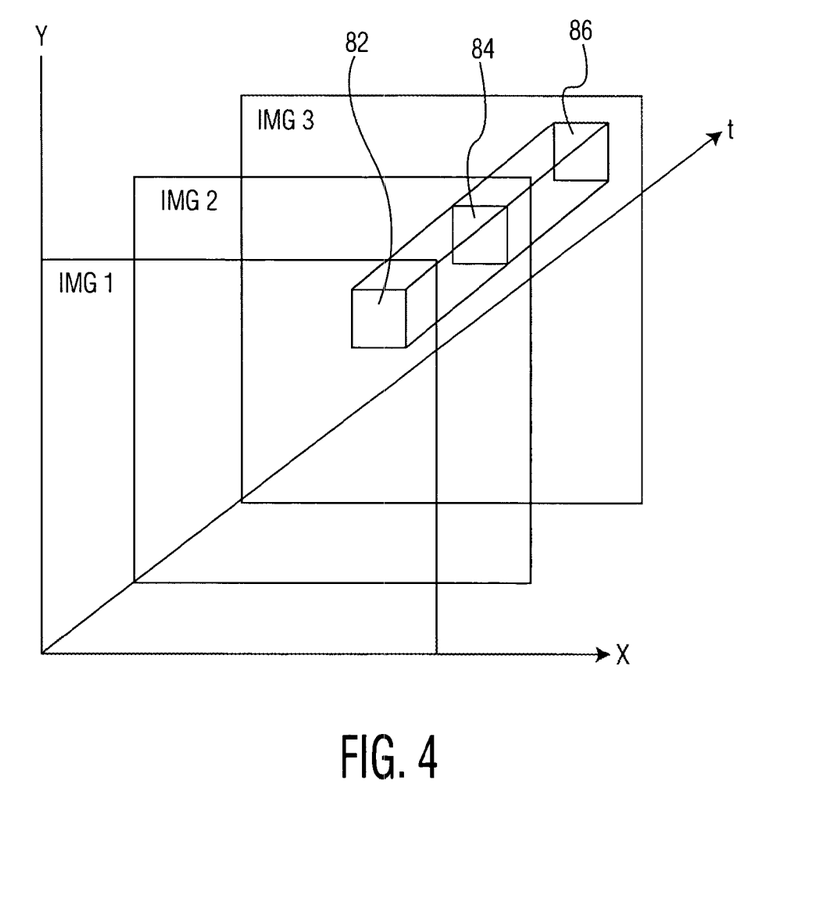
FIG. 4 illustrates a methodology for analyzing motion in successive ultrasound images.

For a rectangular image the blocks may be oriented in a rectilinear grid pattern. For a sector image such as image 70 of FIG. 3 the blocks can be arranged in a curve-linear fashion according to the curvature of the sector. Motion is then computed between corresponding blocks of successive images, as shown in FIG. 4. In this illustration a block 82 of pixels in Img 1 acquired at one point in time is compared with the neighborhood of a corresponding block 84 of an image Img 2 acquired at a different point in time. The next motion computation uses the block 84 in Img 2 and a corresponding block 86 in image Img 3 acquired at another point in time. For each block a motion vector can be derived by finding the maximal Pearson correlation between the two pixel patterns. The formula for this computation is:

$$\rho = \frac{\sum_{x,y}(I_{t1}(x,y) - \bar{I}_{t1})(I_{t2}(x+d_x, y+d_y) - \bar{I}_{t2})}{\sqrt{\sum_{x,y}(I_{t1}(x,y) - \bar{I}_{t1})^2} \sqrt{\sum_{x,y}(I_{t2}(x+d_x, y+d_y) - \bar{I}_{t2})^2}}$$

where I(x,y) is the pixel intensity at coordinates (x,y), the indices t1 and t2 indicate image frames at different time point, $\bar{I}$ is the average intensity in the pixel block, and ($d_x,d_y$) is the magnitude (distance) and direction of the local motion between two image frames. The correlation value ρ indicates the reliability of the motion vector ($d_x,d_y$).

The motion vectors and/or correlation coefficients for a plurality of blocks are then examined. The motion vectors and/or correlation coefficients for all of the blocks can be examined, or only a selected set of blocks can be used such as those in the center of the image 70. If the magnitude of the motion vectors is large for most blocks, or the correlation value ρ is low for most blocks, the frame rate is increased by incrementing the setting of the Res/Speed control from Res toward Speed. The resultant command from the motion/noise processor 46 to the central controller 28 causes the central controller to change the commands to the probe 12 in a manner which increases the frame rate. One way to do this is to increase the angle or spacing of the beam steering between adjacent beams through a change to the beam steering parameter $T_{st}$. With the beams more widely spaced, fewer beams will be transmitted in the area or volume scanned by the probe which causes the frame rate to increase. That is, with fewer beams to transmit and receive to acquire a frame or volume, the image area can be scanned in less time. The increase in the beam spacing decreases the spatial sampling of the image area or volume, causing a corresponding decrease in image resolution. Another way to do this is to increase the multiline order: instead of receiving one or two receive beams in response to a transmit beam, the point spread function can be changed to receive two or four receive beams in response to each of a lesser number of transmit beams. Yet another possibility is to reduce the number of focal zones of the image. For instance, each pair of consecutive focal zones can be combined into one focal zone, with the focus set at the boundary of the two original zones. Thus, the Res/Speed setting has been adjusted in a direction which tends to increase frame rate (Speed) but with decreased image resolution (Res).

Correspondingly, if the magnitude of the motion vectors is small for most blocks, or the correlation value ρ is high for most blocks, indicating little motion between images, the image quality is increased by changing the setting from Speed to Res. The command from the motion processor 46 to the central controller 28 now effects an increase in the beam density by changing the beam steering parameter $T_{st}$ to transmit a greater number of more closely spaced transmit beams which are properly received by a change of the receive beam parameter $R_{sr}$. The multiline order can also be decreased from four to two or two to one, for instance, for a greater number of transmit beams. The number of focal zones can also be increased by splitting one or more current focal zones into two. These changes will all effect an adjustment of the Res/Speed setting in a direction which tends to increase image resolution (Res) with a decrease in the frame rate (Speed).

As these adjustments are made the position of the marker 66 is changed accordingly in the Res/Speed bar 62. This is generally done by changing the value for the marker which is sent from the motion/noise processor 46 to a graphics processor (not shown) which processes the graphic overlay of the Res/Speed control for display with the ultrasound image.

Figure 5:
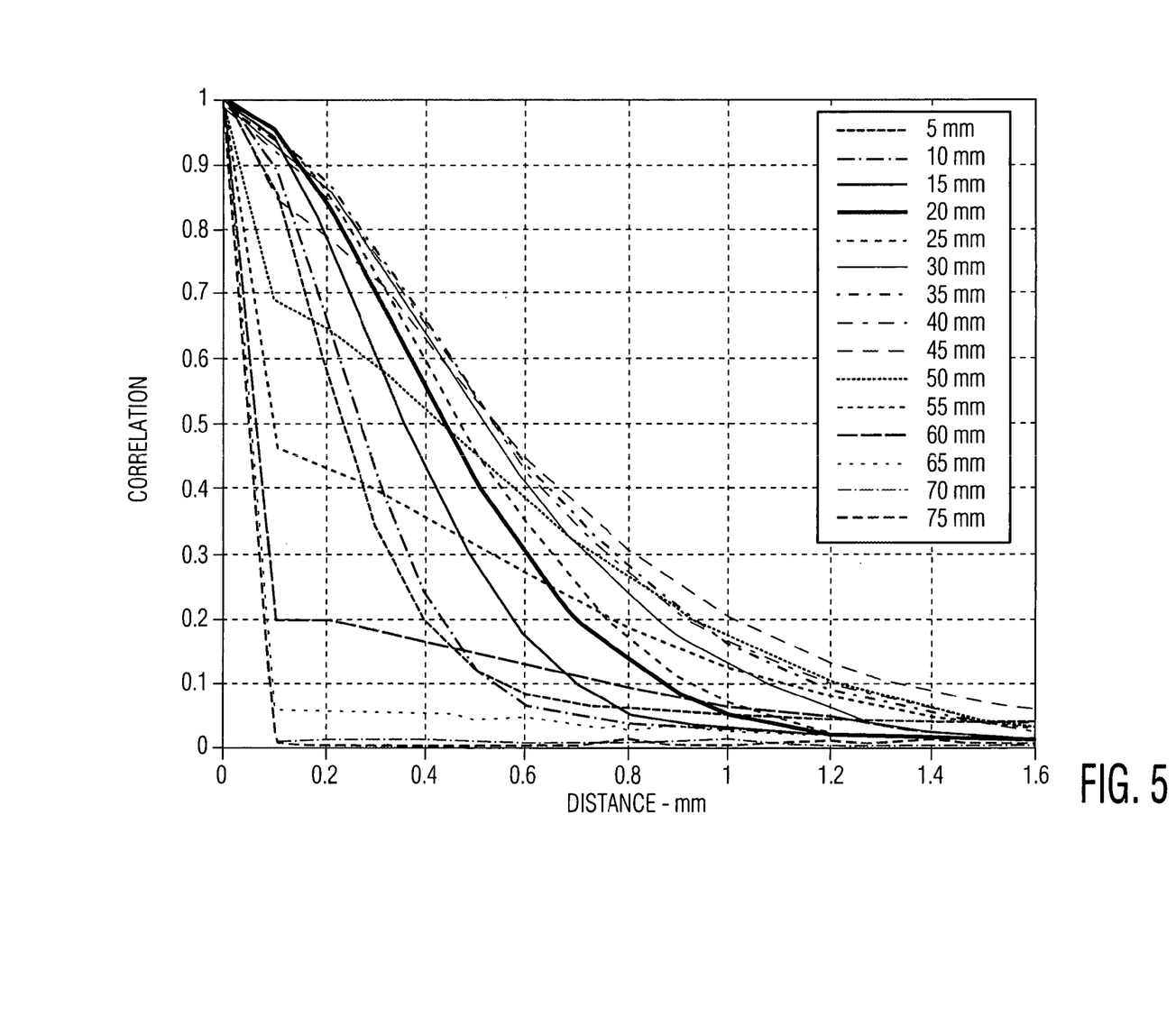
FIG. 5 illustrates the correlation of types of information in successive ultrasound images.

A similar approach can be used to automatically adjust the Pen/Gen/Res control 64 setting as a function of image signal/noise. FIG. 5 illustrates the decorrelation of pure speckle images with motion. This plot is made of the change in correlation as a planar imaging probe travels in the elevational direction. As it does so and the image plane moves in the elevational direction, the speckle information begins to decorrelate over the entire image. In FIG. 5 the X-axis is the distance of travel of the probe in mm and the Y-axis is the correlation between images. The different curves represent the change in correlation at different image depths shown by the legends in box 94. It can be seen that the correlation changes at different rates, depending upon image depth. The solid line curves indicated at 90 for near and mid-field depths show a smooth decline in correlation as the image plane travels, gradually decreasing with increasing distance. However, the dashed curves indicated at 92 for the far field (greater depths) are marked by a sharp drop with a small change in distance, followed by a more gradual decrease. This large initial drop in correlation is believed to be caused by the decorrelation of electronic noise (signal/noise) in the far field and directly related to imaging penetration. A response to a sharp drop in correlation is an adjustment of the Pen/Gen/Res setting toward increased penetration (Pen), as for example by decreasing the transmit frequency or switching from harmonic frequency reception to fundamental frequency reception. See, by comparison, U.S. Pat. No. 6,458,083 (Jago, et al.) and U.S. Pat. No. 6,283,919 (Roundhill et al.) By aligning consecutive image frames through motion compensation and computing the image decorrelation, an appropriate adjustment can be made to the Pen/Gen/Res control to render the best image resolution with optimal imaging penetration. This feature is particularly useful when the clinician is frequently changing the imaging depth during scanning.

Turning again to FIGS. 3 and 4, the correlation is computed for a plurality of pixel blocks 72 of consecutive images. The correlation in the far field is compared with the correlation in the near and/or mid field or the correlation for the entire image. If the correlation is relatively low in the far field and the correlation is relatively high elsewhere, the penetration is increased by adjusting the Pen/Gen/Res control from Res or Gen toward Pen. This effects a command from the motion/noise processor 46 to the central controller 28 which causes the central controller to command a change in the operating frequency. This can be effected by changing the transmit frequency parameter $f_{tr}$ to a lower transmit frequency, reducing the passband of the digital filter 34, or a combination of the two. If blended fundamental/harmonic information is used in the far field, the blending ratio of the two types of signal content can be adjusted in favor of more fundamental signal frequency content. Alternatively, more pulses can be transmitted in each beam direction and greater signal averaging employed. Corresponding, the marker 66 of the Pen/Gen/Res control bar 64 is adjusted toward the Pen end of the control on the displayed graphic.

Similarly, if the correlation is relatively high throughout the image, that is, is not particularly low in the far field, the operating frequency can be increased to increase resolution, and the Pen/Gen/Res control is adjusted from Pen or Gen toward Res. The motion processor commands the central controller 28 to increase the operating frequency by increasing the value of the transmit frequency parameter $f_{tr}$, increasing the passband of the digital filter 34, or both. If blended fundamental/harmonic information is used in the far field, the blending ratio of the two types of signal content can be adjusted in favor of more harmonic signal frequency content. A corresponding adjustment toward Res is made to the marker 66 displayed in the Pen/Gen/Res control 64.

In an embodiment of the present invention, more efficient computation may be obtained by using fewer pixel blocks 72 and the sum of absolute difference (SAD) algorithm. See U.S. Pat. No. 6,442,298 (Olsson et al.) Corresponding pixel blocks of successive images can be compared to compute the motion (displacement) vector from block to block over the time interval between the two images. Then, using this vector, one of the image is warped (aligned) with the other on either a local or global basis. See U.S. Pat. No. 5,566,674 (Weng). This alignment reduces the decorrelation between images due to probe or tissue motion, leaving the signal/noise (electronic noise) factor as a decorrelative effect. The number of pixel blocks used in the alignment computation can be fewer than the number used in the subsequent correlation analysis to reduce computation time, if desired. The correlation of the aligned or warped images is then computed as described above to automatically adjust the Pen/Gen/Res control setting.

What is claimed is:

1. A method for automatically adjusting a relationship between image resolution (Res) and depth of penetration (Pen) of an ultrasound system comprising:
    acquiring a plurality of ultrasound images over time;
    calculating a correlation in a region in a far field of temporally different ultrasound images of the plurality of ultrasound images and a correlation in at least one other region located elsewhere in the temporally different ultrasound images;
    comparing the correlation of the region in the far field with the correlation of the at least one other region to determine a difference in the correlations, wherein the difference in the correlations is due to electronic noise; and
    automatically adjusting image parameters of the ultrasound system based on the comparing, wherein adjusting the image parameters comprises increasing the image resolution if the correlation in the far field is not lower than the correlation in the at least one other region and increasing the depth of penetration if the correlation in the far field is lower than the correlation in the at least one other region, wherein automatically adjusting image parameters comprises:
        adjusting drive signals provided by a transmit frequency control circuit to increase a transmit frequency of an array transducer when the correlation in the far field is not lower than the correlation in the at least one other region, wherein increasing the transmit frequency increases the image resolution of the temporally different ultrasound images; and
        adjusting the drive signals to decrease the transmit frequency when the correlation in the far field is lower than the correlation in the at least one other region, wherein decreasing the transmit frequency increases the penetration.

2. The method of claim 1, wherein the temporally different ultrasound images are successively acquired images and wherein the difference in the correlations is due to a decorrelation of electronic noise in the far field.

3. The method of claim 1, wherein when the comparing shows a relatively low correlation in the far field and a relatively high correlation in the at least one other region, an operating frequency of the ultrasound system is automatically decreased, and when the comparison shows a relatively high correlation in the far field and in the at least one other region, the operating frequency of the ultrasound system is automatically increased.

4. The method of claim 1, wherein increasing the image resolution comprises increasing at least one of the transmit or a receive frequency of the ultrasound system, and wherein increasing the depth of penetration comprises decreasing at least one of the transmit or receive frequency of the ultrasound system.

5. The method of claim 1, further comprising aligning the temporally different ultrasound images prior to calculating the correlations.

6. The method of claim 1, wherein the ultrasound system includes a Pen/Gen/Res control display of the relationship between the image resolution and the depth of penetration; and further comprising automatically adjusting the Pen/Gen/Res control display in correspondence with a change made to a balance between the image resolution and the depth of penetration.

7. The method of claim 6, wherein increasing the image resolution comprises increasing an operating frequency of the ultrasound system; wherein increasing the depth of penetration comprises decreasing the operating frequency of the ultrasound system; and wherein automatically adjusting the Pen/Gen/Res control display comprises adjusting the Pen/Gen/Res control display toward Pen when the operating frequency is decreased and adjusting the Pen/Gen/Res control display toward Res when the operating frequency is increased.

8. The method of claim 7, wherein automatically adjusting the Pen/Gen/Res control display comprises adjusting the Pen/Gen/Res control display toward Pen when fundamental frequency operation is performed and adjusting the Pen/Gen/Res control display toward Res when harmonic operation is performed.

9. The method of claim 7, wherein the operating frequency comprises at least one of the transmit frequency or a receive frequency of the ultrasound system.

10. The method of claim 6, further comprising manually adjusting the Pen/Gen/Res control display to adjust a manner in which automatic adjustments to the balance between resolution and penetration will be made.

11. An ultrasonic diagnostic imaging system comprising:
    a probe including an array transducer;
    a transmit frequency control circuit configured to apply drive signals to the array transducer;
    a receiver configured to process signals received by the array transducer, wherein the receiver includes a B-Mode processor;
    a display coupled to the receiver and configured to display ultrasound images generated from the signals;

a processor coupled to the probe and the transmit frequency control circuit, wherein the processor is configured to:
  calculate a correlation in a region in a far field of the ultrasound images and a correlation in at least one other region located elsewhere in the ultrasound images; and
  compare the correlation of the region in the far field and the correlation of the at least one other region, wherein a difference in the correlations is due to electronic noise; and
a Pen/Gen/Res control display responsive to the processor and which is shown on the display and configured to depict a relative balance between image resolution and penetration of the ultrasound images,
wherein the transmit frequency control circuit is further configured to:
  adjust the drive signals to increase a transmit frequency of the array transducer when the correlation in the far field is not lower than the correlation in the at least one other region, wherein increasing the transmit frequency increases the image resolution of the ultrasound images; and
  adjust the drive signals to decrease the transmit frequency when the correlation in the far field is lower than the correlation in the at least one other region, wherein decreasing the transmit frequency increases the penetration.

12. The method of claim 1, wherein the correlations are calculated using a Pearson correlation.

13. The ultrasonic diagnostic imaging system of claim 11, wherein the difference in the correlations is due to a decorrelation of electronic noise in the far field.

14. The ultrasonic diagnostic imaging system of claim 11, wherein a receiver frequency of the receiver is different than the transmit frequency.

15. The ultrasonic diagnostic imaging system of claim 14, wherein the receiver frequency controlled by the receiver is independently controlled from the transmit frequency controlled by the transmit controller.

16. The ultrasonic diagnostic imaging system of claim 11, wherein the Pen/Gen/Res control display is automatically adjusted in correspondence with a change made to the relative balance between the image resolution and penetration of the ultrasound images.

17. The ultrasonic diagnostic imaging system of claim 16, further comprising a control panel configured to receive a user input for manually adjusting the Pen/Gen/Res control display to adjust a manner in which automatic adjustments to the balance between the image resolution and the penetration will be made.

18. The ultrasonic diagnostic imaging system of claim 11, wherein the correlation is calculated using a Pearson correlation.

\* \* \* \* \*